(12) United States Patent
Ditrich et al.

(10) Patent No.: US 7,358,396 B2
(45) Date of Patent: Apr. 15, 2008

(54) PREPARATION OF OPTICALLY ACTIVE AMINES

(75) Inventors: Klaus Ditrich, Gönnheim (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 187 days.

(21) Appl. No.: 11/327,307

(22) Filed: Jan. 9, 2006

(65) Prior Publication Data

US 2006/0122429 A1 Jun. 8, 2006

Related U.S. Application Data

(62) Division of application No. 10/129,978, filed on May 13, 2002, now Pat. No. 7,078,226.

(51) Int. Cl.
*C07C 233/05* (2006.01)
*C07C 233/65* (2006.01)
*C07C 231/02* (2006.01)
*C12P 41/00* (2006.01)

(52) U.S. Cl. ............ 564/192; 564/134; 564/202; 564/175; 435/280

(58) Field of Classification Search ............ 564/192, 564/202, 175; 435/280
See application file for complete search history.

(56) References Cited

U.S. PATENT DOCUMENTS

| 5,057,607 A | 10/1991 | Zmijewski, Jr. et al. |
| 5,905,167 A | 5/1999 | Ditrich et al. |
| 6,063,615 A * | 5/2000 | Sturmer et al. ............ 435/280 |

FOREIGN PATENT DOCUMENTS

| DE | 247 144 | 1/1911 |
| DE | 723 498 | 8/1942 |
| WO | WO 91/19002 | 12/1991 |
| WO | WO 95/08636 | 3/1995 |
| WO | WO 96/23894 | 8/1996 |
| WO | WO 97/20946 | 6/1997 |
| WO | WO 97/28271 | 8/1997 |
| WO | WO 97/46698 | 12/1997 |
| WO | WO 98/03465 | 1/1998 |
| WO | WO 00/11203 * | 3/2000 |

OTHER PUBLICATIONS

Asensio et al., Tetrahedron Letters 32, 4197-4198, 1991.
Murata et al., J. Chem. Soc. Jpn. Ind. Chem. Sect. 56, 1953:628, Chem. Abstr. 49, 1955, 7517g.
Advanced Organic Chemistry, Reactions, Mechanisms and Structure, Jerry March, 4th Ed., John Wileys & Sons, Inc., 1992, ISBN 0-471-60180-2.
Chem. Abst., vol. 41, No. 19, 10/47. Abst. No. 6199d.
Andres et al., Tetrahedron Letters 33, 20, 1992:2895-2898.
Besse et al., Tetrahedron:Asymmetry, 10, 11, 1999:2213-2224.
Database, Crossfire Beilstein, Database-Accession No. 8253393 (BRN), XP-002171088 & J. Med. Chem., 42, 5, 1999: 833-848.
Database, Crossfire Beilstein, Database-Accession No. 1746407 (BRN), XP-1002171089 & J. Org. Chem., 14, 1949:702.
Database, Crossfire Beilstein, Database-Accession No. 1734381 (BRN), XP-002171090 & Monatsh. Chem., 91, 1960: 363-367.
Database, Crossfire Beilstein, Database-Accession No. 2231657 (BRN), XP-002171091 & Russ. Chem. Bl., 46, 11, 1997: 1936-1938.
Database, Crossfire Beilstein, Database-Accession No. 7174696 (BRN), XP-002171092 & J. Med. Chem., 23, 2, 1980: 121-127.
Database, Crossfire Beilstein, Database Accession No. 1732216 (BRN), XP-002171093 & J. Am. Pharm. Assoc., 41, 1952: 328-332.
Database, Crossfire Beilstein, Database Accession No. 5561939 (BRN), XP-002171094 & J. Org. Chem., 51, 25, 1986: 4905-4910.
Database, Crossfire Beilstein, Database Accession No. 1819513 (BRN), XP-002171095 & Hel. Chim. Acta. 38, 1955:915.
Database, Crossfire Beilstein, Database Accession No. 4304559 (BRN), XP-002171096 & Synth. Commun. 21, 1, 1991: 1-9.
Database, Crossfire Beilstein, Database Accession No. 1919664 (BRN), XP-002171097 & Chem. Pharm. Bull, 18, 1970: 1731-1736.
Kitaguchi et al., J. Amer. Chem. Soc. 111, 3094-3095, 1989.
Gotor et al., J. Chem. Soc. Chem. Commun. 957-958, 1988.
Brieva et al., J. Chem. Soc. Chem. Commun. 1386-1387, 1990.
Quiros et al., J. Chem. Soc. Chem. Commun. 1386-1387, 1990.

* cited by examiner

*Primary Examiner*—Shailendra Kumar
(74) *Attorney, Agent, or Firm*—Novak Druce + Quigg LLP

(57) ABSTRACT

A process for preparing optically active amines, a process for preparing racemic amines which can be resolved using optically active carboxylic acids or enzymes, and racemic and optically active amines and optically active amides are described.

2 Claims, No Drawings

PREPARATION OF OPTICALLY ACTIVE AMINES

This is a Divisional application of application Ser. No. 10/129,978, filed on May 13, 2002 (now U.S. Pat. No. 7,078,226 B1), the entire disclosure of which is hereby incorporated by reference.

The present invention relates to a process for preparing optically active amines. Furthermore, the invention relates to a process for preparing racemic amines which can be resolved using optically active carboxylic acids or enzymes. Moreover, the invention relates to racemic and optically active amines and optically active amides.

Racemate resolution of amines by enzyme-catalyzed reaction with esters, like the classical chemical racemate resolution via formation of diastereomeric salts using optically active carboxylic acids (Advanced Organic Chemistry, Reactions, Mechanisms and Structure, Jerry March, Fourth Edition, John Wiley & Sons, Inc., 1992, ISBN 0-471-60180-2), is known. Thus, Kitaguchi et al. (J. Amer. Chem. Soc. 111 (1989), 3094-3095), for example, describes racemate resolution of amines using trifluoroethyl butyrate under subtilisin catalysis. However, the enantioselectivity of this reaction is highly solvent-dependent. Even when the most suitable of the solvents described (3-methyl-3-pentanol) is used, the selectivity achieved is only moderate.

WO 91/19002 describes a process for chiral enrichment of asymmetric primary amines where the amines are reacted with ethyl acetate or ethyl butyrate under subtilisin catalysis. However, the enantiomeric excesses achieved are unsatisfactory; moreover, long reaction times of from one to a number of weeks are required.

Gotor et al. (J. Chem. Soc. Chem. Commun. (1988), 957-958) describe the enantioselective acylation of 2-amino-butan-1-ol with ethyl acetate under catalysis with porcine pancreas lipase (PPL). Here, the ester used (ethyl acetate) also acts as solvent. If other solvents or other enzymes are used, the results are unsatisfactory.

Brieva et al. (J. Chem. Soc. Chem. Commun. (1990), 1386-1387) describe the enantioselective synthesis of amides from racemic primary amines by reaction with 2-chloropropionate under subtilisin catalysis in hexane or Candida cylindracea lipase catalysis in 3-methyl-3-pentanol.

Quiros et al. (Tetrahedron: Asymmetry 4 (1993), 1105-1112) describe the lipase-catalyzed synthesis of optically active amides from racemic α-halo-substituted ethyl propionates and primary amines. However, the enantioselectivity achieved in this reaction is unsatisfactory.

Asensio et al. (Tetrahedron Letters 32 (1991), 4197-4198) describe the lipase-catalyzed enantioselective acylation of secondary amines. However, this reaction is enantioselective only for one amine, and even there with only moderate results. Other amines are not enantioselective at all.

U.S. Pat. No. 5,057,607 describes the N-acylation of 3-amidoazetdinone [sic] compounds with the aid of penicillin G amidase. However, penicillin G amidase has a very limited substrate range, so that it can only be used for preparing β-lactams.

WO 95/08636 describes a process for racemate resolution of primary and secondary amines by enzyme-catalyzed acylation. Other publications describing processes for enzyme-catalyzed racemate resolution of amines are, for example, WO 96/23894, WO 97/20946, WO 97/2871, WO 97/46698 and WO 98/03465.

The publications mentioned above describe various methods for racemate resolution of amines. In addition to the actual product of value, in each racemate resolution 50% of the unwanted enantiomer are formed. For an economical utilization of these processes it is important that this unwanted enantiomer can be racemized and recycled into the racemate resolution process, or else that this initially unwanted enantiomer is likewise a compound in demand for chemical syntheses and accordingly a product of value. In the enzymatic racemate resolution, one of the enantiomers is obtained in the form of the amide. If this amide is the product of value, it has to be cleaved with the stereocenter being retained. Such a process for cleaving optically active amides while retaining the stereocenter is described, for example, in U.S. Pat. No. 5,905,167.

The provision of the racemic aminoalcohol which is used as starting material for the racemate resolution continues to be an essential problem for the industrial racemate resolution of optically active functionalized amines, such as aminoalcohols. For an economical process, a simple, safe and inexpensive synthetic route to the racemic functionalized amine is required. Murata et al. (J. Chem. Soc. Jpn., Ind. Chem. Sect. 56 (1953): 628, Chem. Abstr. 49 (1955), 7517 g) describe a process for preparing 1-benzyloxy-3-butanone from 3-buten-2-one using 3 equivalents of benzyl alcohol and 0.04 mol % of Na methoxide. This method has the disadvantage that the excess benzyl alcohol has to be removed in an additional process step. Moreover, when carrying out the process, the product is frequently cleaved again into the starting materials, i.e. the consistency required for an industrial process is missing.

The prior-art processes for racemate resolution and the synthesis of the racemic functionalized amines have the disadvantage that they lack the simplicity and consistency required for industrial utilization and that, accordingly, they can only be carried out under highly specific conditions. Moreover, they require considerable amounts of starting materials for the synthesis of the racemic educt, making a process based thereon uneconomical.

It is an object of the present invention to provide a process for synthesizing racemic functionalized amines, such as amino alcohols, and a process based thereon for the racemate resolution of the racemic amines which ensures high consistency and high enantioselectivity in the racemate resolution and can be used in a wide range of reaction conditions, using relatively low amounts of starting material and catalyst, thus lowering the costs of the overall process even further.

We have found that this object is achieved by a process for preparing compounds of the formula I

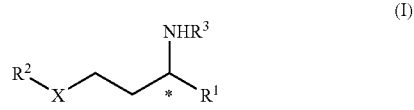

\* = optically active which comprises the following process steps:
a) A reaction of compounds of the formula II

with compounds of the formula R²—XH (III) in the presence of a base to give compounds of the formula IV

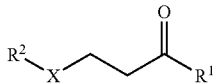

(IV)

b) A reaction of the reaction solution of compounds of the formula IV with a compound of the formula NH₂R³ (V) to give compounds of the formula VI

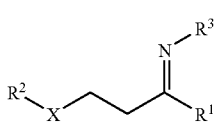

(VI)

c) A hydrogenation of compounds of the formula VI in the presence of a hydrogenation catalyst to give compounds of the formula VII

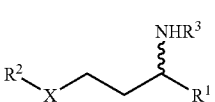

(VII)

d) A resolution of a racemate of compounds of the formula VII using an optically active carboxylic acid or esters of the formula VIII

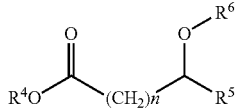

(VIII)

in the presence of a lipase or esterase, giving compounds of the formula I where the substituents and variables in the formulae I, II, III, IV, V, VI, VII and VIII are as defined below:

$R^1$ is substituted or unsubstituted, branched or unbranched $C_1$-$C_{10}$-alkyl, $C_2$-$C_{10}$-alkenyl, $C_2$-$C_{10}$-alkynyl, arylalkyl, aryl, hetarylalkyl or hetaryl, $R^2$ is substituted or unsubstituted, branched or unbranched $C_1$-$C_{10}$-alkyl, $C_3$-$C_{10}$-alkenyl, $C_3$-$C_{10}$-alkynyl, arylalkyl, aryl, hetarylalkyl or hetaryl, $R^3$ is hydrogen, hydroxyl, substituted or unsubstituted, branched or unbranched $C_1$-$C_{10}$-alkyl, $C_3$-$C_{10}$-alkenyl or $C_3$-$C_{10}$-alkynyl, $R^4$ is substituted or unsubstituted, branched or unbranched $C_1$-$C_{10}$-alkyl, $R^5$ is hydrogen, substituted or unsubstituted, branched or unbranched $C_1$-$C_{10}$-alkyl, $R^6$ is hydrogen, substituted or unsubstituted, branched or unbranched $C_1$-$C_{10}$-alkyl or substituted or unsubstituted phenyl, X=oxygen or nitrogen, preferably nitrogen n=0 or 1.

In the compounds of the formulae I, II, IV, VI, VII and IX, $R^1$ is substituted or unsubstituted, branched or unbranched $C_1$-$C_{10}$-alkyl, $C_2$-$C_{10}$-alkenyl, $C_2$-$C_{10}$-alkinyl, arylalkyl, aryl, hetarylalkyl or hetaryl. Preferred radicals of $R^1$ are substituted or unsubstituted, branched or unbranched $C_1$-$C_{10}$-alkyl or aryl.

Alkyl radicals which may be mentioned are substituted or unsubstituted, branched or unbranched $C_1$-$C_{10}$-alkyl chains, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals are methyl, ethyl or propyl.

Alkenyl radicals which may be mentioned are branched or unbranched $C_2$-$C_{10}$-alkenyl chains, such as, for example, ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl or decenyl.

Alkynyl radicals which may be mentioned are branched or unbranched $C_2$-$C_{10}$-alkynyl chains, such as, for example, ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl.

Advantageously, the multiple bond of the alkenyl or alkynyl radicals should not be in the position alpha to the carbonylcarbon since this would have an adverse effect on the selectivity of the reaction [process step (a)] and may necessitate a purification of the reaction products. In this case, the selectivity can be influenced positively by electron-donating and/or bulky radicals, such as tert-butyl.

Suitable substituents of the abovementioned radicals of $R^1$ are, in principle, all feasible substituents except for ketones or aldehydes, for example one or more substituents such as halogen, for example fluorine, amino, hydroxyl, alkyl, cycloalkyl, aryl, alkoxy, benzyloxy, phenyl or benzyl.

Arylalkyl radicals which may be mentioned are branched or straight-chain phenyl-($C_1$-$C_5$-alkyl) or naphthyl-($C_1$-$C_5$-alkyl) radicals, such as phenylmethyl, phenylethyl, phenylpropyl, phenyl-1-methylethyl, phenylbutyl, phenyl-1-methylpropyl, phenyl-2-methylpropyl, phenyl-1,1-dimethylethyl, phenylpentyl, phenyl-1-methylbutyl, phenyl-2-methylbutyl, phenyl-3-methylbutyl, phenyl-2,2-dimethylpropyl, phenyl-1-ethylpropyl, naphthylmethyl, naphthylethyl, naphthylpropyl, naphthyl-1-methylethyl, naphthylbutyl, naphthyl-1-methylpropyl, naphthyl-2-methylpropyl, naphthyl-1,1-dimethylethyl, naphthylpentyl, naphthyl-1-methylbutyl, naphthyl-2-methylbutyl, naphthyl-3-methylbutyl, naphthyl-2,2-dimethylpropyl, or naphthyl-1-ethylpropyl, and their isomeric or stereoisomeric forms. Preferred radicals are branched or straight-chain phenyl-($C_1$-$C_5$-alkyl) radicals, such as phenylmethyl, phenylethyl or phenylpropyl.

Aryl radicals which may be mentioned are, for example, phenyl, methoxyphenyl or naphthyl, or aromatic rings or ring systems having 6 to 18 carbon atoms in the ring system and up to 24 other carbon atoms which may form other non-aromatic rings or ring systems having 3 to 8 carbon atoms, which may be unsubstituted or substituted by one or more radicals, such as halogen, for example fluorine, amino, hydroxyl, alkyl, alkoxy or other radicals. Preference is given to unsubstituted or substituted phenyl, methoxyphenyl or naphthyl.

Hetaryl(alkyl) radicals which may be mentioned are, for example, hetarylalkyl radicals which contain one or more nitrogen, sulfur and/or oxygen atoms in the ring or ring system and are attached to a branched or unbranched $C_1$-$C_5$-alkylene chain, such as methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene or 1-ethylpropylene.

Hetaryl radicals which may be mentioned are simple or fused aromatic ring systems having one or more heteroaromatic 3- to 7-membered rings which may contain one or more heteroatoms, such as N, O and S, and which may be unsubstituted or substituted by one or more radicals, such as halogen, for example fluorine, amino, hydroxyl, thio, alkyl, alkoxy or other aromatic or other saturated or unsaturated non-aromatic rings or ring systems.

In the compounds of the formulae I, III, IV, VI, VII and IX, $R^2$ is substituted or unsubstituted, branched or unbranched $C_1$-$C_{10}$-alkyl, $C_2$-$C_{10}$-alkenyl, $C_2$-$C_{10}$-alkynyl, arylalkyl, aryl, hetarylalkyl or hetaryl. Preferred radicals of $R^1$ are substituted or unsubstituted, branched or unbranched $C_1$-$C_{10}$-alkyl or arylalkyl.

Alkyl radicals which may be mentioned are substituted or unsubstituted, branched or unbranched $C_1$-$C_{10}$-alkyl chains, such as, for example, methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals are methyl, ethyl or propyl.

Alkenyl radicals which may be mentioned are branched or unbranched $C_3$-$C_{10}$-alkenyl chains, such as, for example, 2-propenyl, 2-butenyl, 3-butenyl, 2-methylpropenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, 2-heptenyl, 3-heptenyl, 4-heptenyl, 5-heptenyl, 6-heptenyl, 2-octenyl, 3-octenyl, 4-octenyl, 5-octenyl, 6-octenyl, 7-octenyl, nonenyl or decenyl. Preferred radicals are 2-propenyl or 2-butenyl.

Alkynyl radicals which may be mentioned are branched or unbranched $C_3$-$C_{10}$-alkynyl chains, such as, for example, prop-2-yn-1-yl, n-but-1-yn-3-yl, n-but-1-yn-4-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl. The preferred radical is prop-2-yn-1-yl.

Suitable substituents of the abovementioned radicals of $R^2$ are, in principle, all feasible substituents, for example one or more substituents such as halogen, for example fluorine, amino, hydroxyl, alkyl, cycloalkyl, aryl, alkoxy, benzyloxy, phenyl or benzyl.

Arylalkyl radicals which may be mentioned are branched or straight-chain phenyl-($C_1$-$C_5$-alkyl) or naphthyl-($C_1$-$C_5$-alkyl) radicals, such as phenylmethyl, phenylethyl, phenylpropyl, phenyl-1-methylethyl, phenylbutyl, phenyl-1-methylpropyl, phenyl-2-methylpropyl, phenyl-1,1-dimethylethyl, phenylpentyl, phenyl-1-methylbutyl, phenyl-2-methylbutyl, phenyl-3-methylbutyl, phenyl-2,2-dimethylpropyl, phenyl-1-ethylpropyl, naphthylmethyl, naphthylethyl, naphthylpropyl, naphthyl-1-methylethyl, naphthylbutyl, naphthyl-1-methylpropyl, naphthyl-2-methylpropyl, naphthyl-1,1-dimethylethyl, naphthylpentyl, naphthyl-1-methylbutyl, naphthyl-2-methylbutyl, naphthyl-3-methylbutyl, naphthyl-2,2-dimethylpropyl, or naphthyl-1-ethylpropyl, and their isomeric or stereoisomeric forms. Preferred radicals are phenylmethyl, phenylethyl or naphthylmethyl.

Aryl radicals which may be mentioned are, for example, phenyl, methoxyphenyl or naphthyl, or aromatic rings or ring systems having 6 to 18 carbon atoms in the ring system and up to 24 other carbon atoms which may form other non-aromatic rings or ring systems having 3 to 8 carbon atoms in the ring, which may be unsubstituted or substituted by one or more radicals, such as halogen, for example fluorine, amino, hydroxyl, alkyl, alkoxy or other radicals. Preference is given to unsubstituted or substituted phenyl, methoxyphenyl or naphthyl.

Hetaryl(alkyl) radicals which may be mentioned are, for example, hetarylalkyl radicals which contain one or more nitrogen, sulfur and/or oxygen atoms in the ring or ring system and are attached to a branched or unbranched $C_1$-$C_5$-alkylene chain, such as methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene or 1-ethylpropylene.

Hetaryl radicals which may be mentioned are simple or fused aromatic ring systems having one or more heteroaromatic 3- to 7-membered rings which may contain one or more heteroatoms, such as N, O and S, and which may be unsubstituted or substituted by one or more radicals, such as halogen, for example fluorine, amino, hydroxyl, thio, alkyl, alkoxy or other aromatic or other saturated or unsaturated non-aromatic rings or ring systems.

In the compounds of the formulae I, V, VI, VII and IX, $R^3$ is hydrogen, hydroxyl, substituted or unsubstituted, branched or unbranched $C_1$-$C_{10}$-alkyl, $C_3$-$C_{10}$-alkenyl or $C_3$-$C_{10}$-alkynyl. Preferred radicals are hydrogen or hydroxyl.

Alkyl radicals which may be mentioned are substituted or unsubstituted, branched or unbranched $C_1$-$C_{10}$-alkyl chains, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals are methyl, ethyl or propyl.

Alkenyl radicals which may be mentioned are branched and unbranched $C_3$-$C_{10}$-alkenyl chains, such as, for example, propenyl, 2-butenyl, 3-butenyl, 2-methylpropenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, 2-heptenyl, 3-heptenyl, 4-heptenyl, 5-heptenyl, 6-heptenyl, 2-octenyl, 3-octenyl, 4-octenyl, 5-octenyl, 6-octenyl, 7-octenyl, nonenyl or decenyl.

Alkynyl radicals which may be mentioned are branched or unbranched $C_3$-$C_{10}$-alkynyl chains, such as, for example, prop-2-yn-1-yl, n-but-1-yn-3-yl, n-but-1-yn-4-yl, n-but-2-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl.

Suitable substituents of the abovementioned radicals of $R^3$ are, in principle, all feasible substituents, for example one or more substituents such as halogen, for example fluorine, amino, hydroxy, alkyl, cycloalkyl, aryl, alkoxy, benzyloxy, phenyl or benzyl.

In the compounds of the formula VIII, $R^4$ is substituted or unsubstituted, branched or unbranched $C_1$-$C_{10}$-alkyl.

Alkyl radicals which may be mentioned are substituted or unsubstituted, branched or unbranched $C_1$-$C_{10}$-alkyl chains, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals are methyl, ethyl, 1-methylethyl, propyl, butyl or pentyl.

Suitable substituents of the abovementioned radicals of $R^4$ are, in principle, all feasible substituents, for example one or more substituents such as halogen, for example fluorine, chlorine or bromine, cyano, nitro, amino, hydroxyl, alkyl, cycloalkyl, aryl, alkoxy, benzyloxy, phenyl or benzyl. Preferred substituents are halogen, such as chlorine or bromine, cyano, benzyloxy, $C_1$-$C_4$-alkyl or hydroxyl.

In the compounds of the formulae VIII and IX, $R^5$ is hydrogen, substituted or unsubstituted, branched or unbranched $C_1$-$C_{10}$-alkyl.

Alkyl radicals which may be mentioned are substituted or unsubstituted, branched or unbranched $C_1$-$C_{10}$-alkyl chains, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals are hydrogen, methyl, ethyl or propyl.

Suitable substituents of the abovementioned radicals of $R^5$ are, in principle, all feasible substituents, for example one or more substituents such as halogen, for example fluorine, chlorine or bromine, cyano, nitro, amino, hydroxyl, alkyl, cycloalkyl, aryl, alkoxy, benzyloxy, phenyl or benzyl.

In the compounds of the formulae VIII and IX, $R^6$ is hydrogen, substituted or unsubstituted, branched or unbranched $C_1$-$C_{10}$-alkyl or substituted or unsubstituted phenyl.

Alkyl radicals which may be mentioned are substituted or unsubstituted, branched or unbranched $C_1$-$C_{10}$-alkyl chains, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Preferred radicals are methyl, ethyl or propyl.

Suitable substituents of the abovementioned radicals of $R^6$ are, in principle, all feasible substituents, for example one or more substituents such as halogen, for example fluorine, chlorine or bromine, cyano, nitro, amino, hydroxyl, alkyl, cycloalkyl, aryl, alkoxy, benzyloxy, phenyl or benzyl.

The invention furthermore relates to a process for preparing compounds of the formula VII

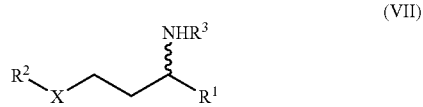

which comprises the following process steps:
a) A reaction of compounds of the formula II

with compounds of the formula $R^2$—XH (III) in the presence of a base to give compounds of the formula IV

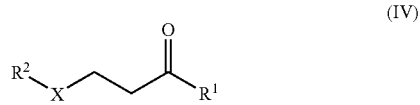

b) A reaction of the reaction solution of compounds of the formula IV with a compound of the formula $NH_2R^3$ (V) to give compounds of the formula VI

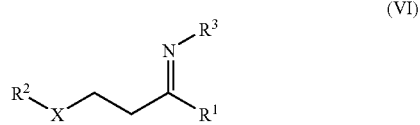

c) A hydrogenation of compounds of the formula VI in the presence of a hydrogenation catalyst to give compounds of the formula VII, where the substituents and variables in the formulae II, III, IV, V, VI and VII are as defined in claim 1.

For clarity, scheme I shows the processes according to the invention in an exemplary manner. Process steps (a) to (d) correspond to the process for preparing functionalized optically active amines, for example optically active aminoalcohols or optically active diamines. The process steps (a) to (c) correspond to the process for preparing functionalized racemic amines which can subsequently be subjected to racemate resolution. In scheme I, this racemate resolution is shown using the example of enzymatic racemate resolution. However, it can also be carried out using other processes for racemate resolution, such as the classical chemical racemate resolution via diastereomeric salts, or via chromatographic processes. The variables and substituents used in scheme I are as defined above. The scheme furthermore shows the optional possibility of neutralizing the reaction solution obtained in step (a) prior to the reaction with compounds of the structure or formula $NH_2R^3$ (V). If the compounds of the formula $R^2$—XH (III) are employed in a large excess, based on the reaction partner (II), it is necessary to neutralize the reaction solution prior to further reaction, since otherwise an undesirable cleavage of the reaction product into the starting materials occurs when the excess compound $R^2$—XH is removed. This cleavage results in a loss of yield, and the product has to be purified. If the advantageous amount, according to the invention, of the compound (III) of from 0.5 to 2.5 equivalents, preferably from 0.5 to 2.0; particularly preferably from 0.7 to 1.5; very particularly preferably from 0.9 to 1.1 equivalents, based on the reaction partner (II), is employed, it is not necessary to reduce the amount of excess $R^2$—XH, and neutralization of the reaction solution prior to the reaction step b is advantageously not necessary in the processes according to the invention. However, depending on the starting materials, neutralization may advantageously be carried out to increase the consistency of the process. Acids suitable for the neutralization are all customary mineral acids, such as HCl, $H_2SO_4$ or $H_3PO_4$, or organic acids, such as lower aliphatic carboxylic acids, for example formic acid. Preference is given to using orthophosphoric acid.

Suitable bases for process step (a) of the process according to the invention are, in principle, all bases which can catalyze the addition of the compound (III) to the Michael system of the compound (II), such as NaOH, KOH, tertiary amines or alkali metal alkoxides or alkaline earth metal alkoxides. Bases which may be mentioned as being advantageous are alkali metal alkoxides and alkaline earth metal alkoxides, such as sodium methoxide, sodium ethoxide, sodium butoxide, sodium tert-butoxide, potassium tert-butoxide, or strong basic amines, such as diazabicycloundecene. As catalyst, the base is advantageously employed in a concentration of from 0.001 to 10 mol %, preferably from 0.01 to 5 mol %, particularly preferably from 0.3 to 0.5 mol %, based on the compound (III) used.

Process step (a) of the processes according to the invention can be carried out in the presence of an aprotic solvent which is inert under the reaction conditions. Examples of suitable solvents are hydrocarbons, such as hexane, cyclohexane, benzene or toluene, or ethers, such as methyl tert-butyl ether (=MTBE), diethyl ether, dibutyl ether or tetrahydrofuran (=THF). The reaction is advantageously carried out in the absence of a solvent.

The reaction [process step (a)] is advantageously carried out at from –30 to +50° C., preferably from –5 to +10° C.

Advantageous compounds of the formula (V) are, in addition to ammonia, primary and secondary aliphatic amines and hydroxylamine. Process step (b) is advantageously carried out using hydroxylamine, which is employed as aqueous solution, or as an aqueous solution of its salt, such as, for example, hydroxylamine hydrochloride, hydroxylamine sulfate, if appropriate, as for the other compounds of the formula (V), in the presence of a base, such as aqueous sodium hydroxide solution or sodium acetate. Preference is given to using an aqueous solution of the free hydroxylamine. The reaction can advantageously be carried out in an inert protic solvent, such as water or an alcohol, for example methanol, ethanol, propanol, butanol or isobutanol. The reaction is preferably carried out in water.

The reaction [process step (b)] is advantageously carried out at from 0 to +100° C., preferably from 20 to 40° C.

The hydrogenation in the processes according to the invention [process step (c)] can be carried out using all customary hydrogenation catalysts based, for example, on Ni, Co, Hg, Pt, Pd, Ru or Rh. One of the catalysts customarily used for homogeneous catalysis is, for example, Wilkinson's catalyst. The hydrogenation can be carried out under heterogeneous or homogeneous catalysis. For economical reasons and because it is readily available, the preferred catalyst is Raney nickel. The hydrogenation is advantageously carried out in a solvent which is inert under the reaction conditions. Such solvents are, for example, hydrocarbons, such as hexane, cyclohexane, benzene or toluene, ethers, such as MTBE, diethyl ether, dibutyl ether or THF, or alcohols, such as methanol, ethanol, propanol, butanol or iso-butanol. Preferred solvents are THF or methanol.

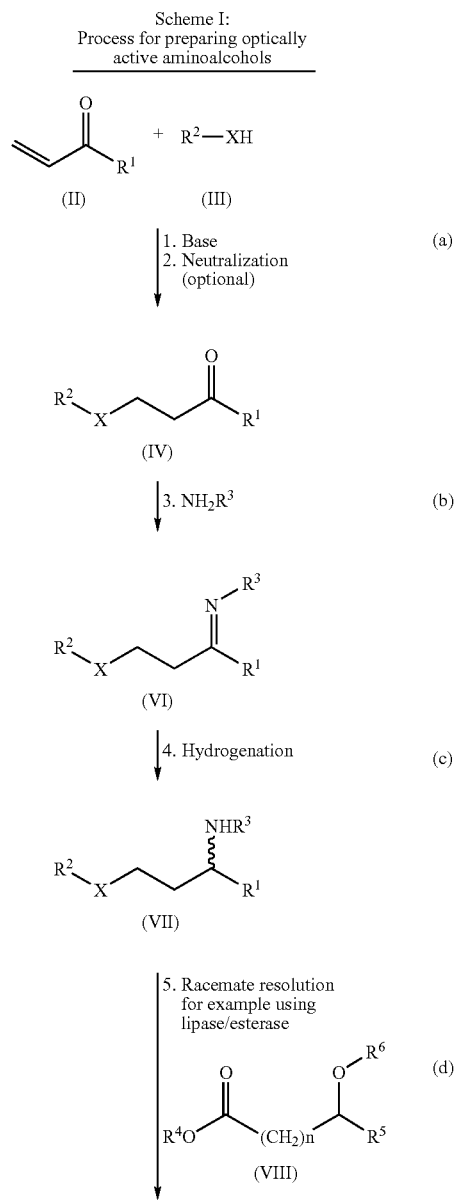

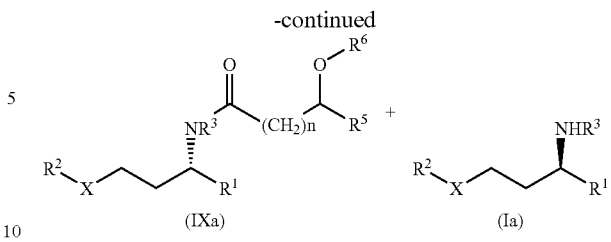

The reaction [process step (c)] is advantageously carried out at from 0 to +150° C., preferably from 50 to 100° C. The hydrogenation is usually carried out in a pressure range of from atmospheric pressure to 300 bar. The reaction is preferably carried out at a pressure of from 50 to 150 bar.

As described above, the racemate resolution can be carried out via enzymatic or classical chemical racemate resolution, including the use of chromatographic methods. The racemate resolution is preferably carried out with the aid of enzymes or diastereomeric salts, particularly preferably using enzymes.

For the separation via diastereomeric salts, all optically active carboxylic acids are suitable in principle. Advantageous optically active carboxylic acids are tartaric acid, dibenzoyltartaric acid, mandelic acid, camphoric acid, camphorsulfonic acid, p-hydroxymandelic acid, p-Cl-mandelic acid, phenoxypropionic acid, p-hydroxyphenoxypropionic acid or lactic acid. Preference is given to using mandelic acid for the racemate resolution. The salt formation can be carried out in an inert solvent, such as a hydrocarbon, for example hexane, cyclohexane, benzene or toluene; or an ether, for example MTBE, diethyl ether, dibutyl ether or THF; or an alcohol, for example methanol, ethanol, propanol, isopropanol, butanol or isobutanol. For recrystallization, it is advantageous to employ an alcohol, such as methanol, ethanol, propanol, isopropanol, butanol or isobutanol. Preference is given to using isopropanol. To improve crystallization, the solution can be cooled. If the salt formed precipitates spontaneously, it is redissolved by heating and slowly recrystallized with cooling. If required, the crystallization can be carried out a number of times.

The racemate resolution of the functionalized amines can advantageously also be carried out via enzymes such as esterases or lipases.

Esterases and lipases which are suitable for the process according to the invention are, in principle, all lipases and esterases available from plants, animals or microorganisms. It is advantageous to use microbial lipases which can be isolated, for example, from eucaryotic organisms, such as fungi or yeasts, or procaryotic organisms, such as bacteria. Bacterial lipases from the genera *Bacillus* or *Pseudomonas*, for example Amano P or the lipase from *Pseudomonas* spec. DSM 8246, or lipases from fungi such as *Aspergillus* or from yeasts such as *Candida* or *Yerrowia*, are particularly suitable. Further advantageous lipases are, for example, the enzymes which are commercially available from Novo Nordisk, in particular the lipases SP 523, SP 524, SP 525, SP 526 and Novozym® 435, which are obtained from yeasts, such as *Candida antarctica*. Other examples are the lipases Chirazyme L1, L2, L3, L4, L5, L6, L7 and L8 which are commercially available from Roche Molecular Biochemicals (Roche Diagnostic GmbH, Penzberg).

The lipases can be employed in native or immobilized form. The immobilized lipases can be microencapsulated, emulsified with prepolymers and polymerized, crosslinked with bifunctional substances (oligomers, aldehydes etc.) or attached to inorganic or organic carriers, such as, for example, Celite, Lewatit, zeolites, polysaccharides, polyamides or polystyrene resins. Particular preference is given to the lipases Novozym® 435 and Chirazyme L2.

The reaction with the esterases or lipases is generally carried out under atmospheric pressure, if appropriate under inert gas, such as nitrogen or argon. However, it can also be carried out under elevated pressure.

The temperature for the reaction of the racemic amines of the formula VII with the esters suitable for the racemate resolution, which carry an oxygen atom in the position alpha to the carbonyl carbon, specifically the esters of the formula VIII

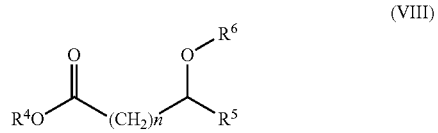

is usually from 0 to 90° C., preferably from 10 to 60° C., particularly preferably from 20 to 50° C. The substituents of the preferred esters VIII are as defined above.

The reaction of the ester with the racemic functionalized amine, i.e. the corresponding aminoalcohol or diamine, under enzyme catalysis is usually carried out at room temperature. Depending on the substrate, the reaction times are from 1 to 48 hours. Secondary aminoalcohols or diamines generally require longer reaction times than primary aminoalcohols or diamines. The lower reactivity of secondary amines can also be compensated by an increased amount of catalyst, compared to primary amines.

From 0.5 to 2.0 mol, preferably from 0.5 to 1 mol, of ester are employed per mole of racemic amine. The amount of enzyme required depends on the activity of the enzyme preparation and the reactivity of the amine and can easily be determined by preliminary experiments. In general, from 0.1 to 10% by weight, preferably from 1 to 5% by weight, of the immobilized enzyme preparation (based on the racemic amine) are employed. Novozym® 435 has an activity of about 7000 PL U/g-10,000 PL U/g (PL=propyl laurate units, the units are based on the substrate propyl laurate).

The amount of enzyme that has to be added depends on the type of enzyme and the activity of the enzyme preparation. The optimum amount of enzyme for the reaction can easily be determined by simple preliminary experiments.

The course of the reaction can easily be monitored by customary methods, such as gas chromatography or high pressure liquid chromatography. If the desired conversion, generally 50%, has been achieved, the reaction is terminated, preferably by removing the catalyst, for example by filtering off the (supported) enzyme. The reaction can also be terminated, for example, by addition of enzyme-destroying substances, such as acids or bases, or by heating. If the reaction is carried out continuously, the conversion can be controlled by the enzyme load, i.e. the amount of amine which is pumped through the enzyme reactor per time unit. The process can preferably be carried out continuously, but also batch-wise or semi-continuously.

The enzyme-catalyzed racemate resolution can be carried out in protic or aprotic solvents or else without addition of solvents. Suitable solvents are, for example, hydrocarbons such as hexane, cyclohexane or toluene, ethers, such as, for example, diethyl ether, dioxane, methyl tert-butyl ether, tert-amyl methyl ether or THF, nitrites, such as acetonitrile, butyronitrile, alcohols, such as tert-butanol, 3-methyl-3-pentanol, and halogenated hydrocarbons, such as, for example, methylene chloride.

The reaction proceeds particularly well when the solvents and starting materials are as anhydrous as possible. For the racemate resolution, the solvents and starting materials amine and ester are advantageously dried. In principle this can be carried out in any manner known to the person skilled in the art, for example by azeotropic drying or by using drying agents, such as sodium sulfate, magnesium sulfate, KOH, phosphorus pentoxide, molecular sieves, silica gel or alumina.

After the enzyme-catalyzed racemate resolution has ended, a mixture of the acylated amine enantiomer of the formula IX

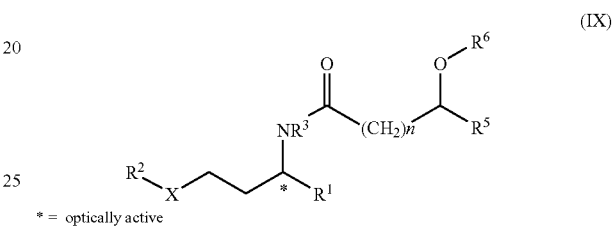

* = optically active the unreacted amine enantiomer, the alcohol released from the ester during acylation and possibly excess ester is present. Suitable for separating this mixture are, in particular, distillative and extractive methods. Thus, low-boiling amines can be distilled off directly from the reaction mixture. The amide can subsequently be separated off distillatively or extractively from the alcohol and, if appropriate, the ester and can then be hydrolyzed in a customary manner, for example by boiling with aqueous sodium hydroxide or potassium hydroxide solution, with racemization or else without racemization (see U.S. Pat. No. 5,905,167). In columns 2 to 5 and in Example 2, U.S. Pat. No. 5,905,167 describes a method for cleaving amides with retention of the stereocenter. The second amine enantiomer formed in the hydrolysis can be isolated distillatively or extractively from the carboxylic acid, which is present as a salt. The isolation is preferably carried out by extraction, using, as extractant, ethers, such as diethyl ether, methyl tert-butyl ether and dibutyl ether, halogenated hydrocarbons, such as dichloromethane or trichloroethylene, or hydrocarbons, such as pentane, hexane, cyclohexane, benzene, toluene and xylene. A likewise preferred embodiment of the isolation of the amine is steam distillation. A particularly suitable embodiment of the invention comprises carrying out the cleavage at a temperature which is sufficiently high to distil over the resulting reaction product (amine) together with the steam, so that it is removed immediately from the reaction mixture, whereas the acid, which is dissociated under the alkaline conditions, remains in the flask. By the routes mentioned, it is, in principle, possible to work up amines in the processes according to the invention.

The resulting free amine can either be used as a further product of value for further syntheses or else advantageously be recycled after racemization into the process at the stage of process step (d). The amide cleaved directly with racemization can likewise advantageously be recycled into the process at this stage. In this manner, it is theoretically possible to convert the entire racemate into the desired enantiomer. Such racemizations can be carried out, for example, under the same conditions which are used for preparing amines from alcohols or ketones ("reductive amination"). The acid formed during the hydrolysis can, after acidification of the hydrolysis solution, be recovered, preferably extractively, and esterified by customary processes and recycled.

The processes according to the invention are advantageously suitable for preparing racemic aminoalcohols of the formula Ic and for resolving their racemate via enantioselective acylation

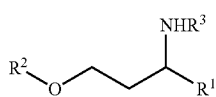

(Ic)

in which the substituents are as defined above.

The invention furthermore relates to compounds of the formula I, VII and IX:

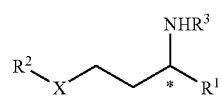

(I)

* = optically active

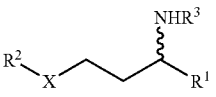

(VII)

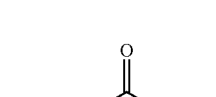

(IX)

* = optically active in which the substituents and variables in the formulae I, VII and IX are as defined above. Preferred compounds of the formulae I, VII and IX are the following compounds:

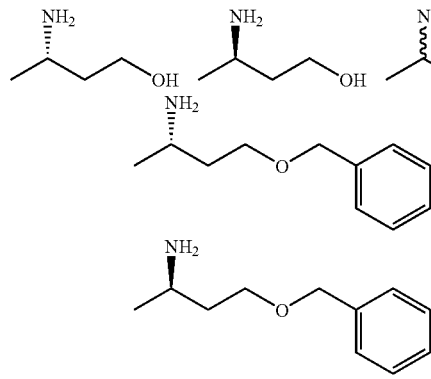

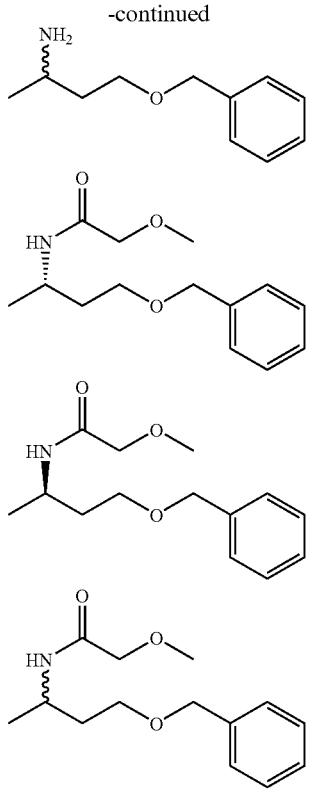

The processes according to the invention are not only suitable as preparation processes for producing optically active primary and secondary functionalized amines, such as aminoalcohols or diamines, but they can also be a component of complicated chemical multi-step syntheses, for example in the preparation of drugs or crop protection agents.

The examples below serve to illustrate the invention.

EXAMPLES

Scheme II:
Process for preparing R- and
S-1-benzyloxy-3-aminobutane
( = rac. BOBA)

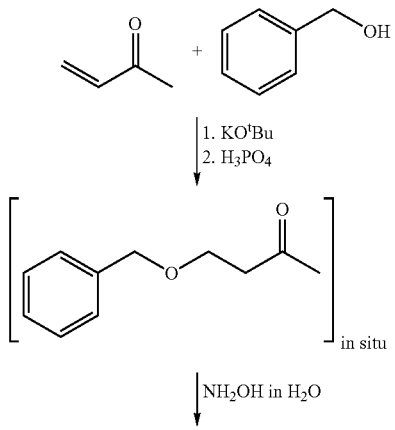

-continued

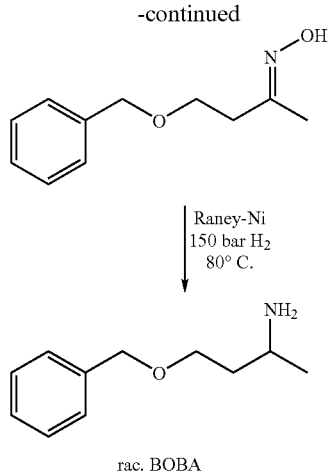

rac. BOBA

Example 1

Process Steps (a) and (b): Synthesis of
1-benzyloxy-3-butanoneoxime (Scheme III)

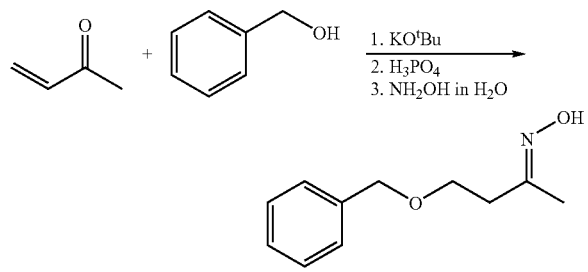

At 0° C., 648 g (6.0 mol) of benzyl alcohol were admixed with 2.6 g (24 mmol) of potassium tert-butoxide, and the mixture was stirred for 30 minutes. Over a period of 30 minutes, 441 g (6.3 mol) of freshly distilled methyl vinyl ketone were added dropwise, the temperature being maintained at 0-10° C. by cooling. After the addition had ended, the mixture was stirred at 10° C. for another hour. 2.8 g (24 mmol) of orthophosphoric acid (as an 85% strength aqueous solution) were then added dropwise. The mixture was warmed to room temperature (=23° C.).

According to $^1$H-NMR, 1-benzyloxy-3-butanone was formed in the reaction ($^1$H-NMR: δ=2.05 (s; 3H), 2.60 (t, J=7.0 Hz; 2H), 3.65 (t, J=7.0 Hz; 2H), 4.45 (s, 2H), 7.25 (m, 5H).

With vigorous stirring, 471 g of a 51.7% strength aqueous solution (7.37 mol) of hydroxylamine were added dropwise to the crude 1-benzyloxy-3-butanone such that the reaction temperature remained at about 35° C. The mixture was then stirred for another 15 hours. The next day, the upper, aqueous phase was separated off and the lower, organic phase was taken up in 500 ml of toluene and heated on a water separator until no more water distilled over. The solvent and volatile components were distilled off at 0.5 mm (bath temperature: 100° C.), giving as a residue 1100 g (95%) of 1-benzyloxy-3-butanoneoxime as E/Z mixture.

Main Isomer (about 65%):
$^1$H-NMR: δ=1.90 (s; 3H), 2.50 (t, J=7.0 Hz; 2H), 3.65 (t, J=7.0 Hz; 2H), 4.50 (s, 2H), 7.30 (m, 5H), 9.30 (s, broad, 1H).

Minor Isomer (about 35%):
$^1$H-NMR: δ=1.95 (s; 3H), 2.75 (t, J=7.0 Hz; 2H), 3.65 (t, J=7.0 Hz; 2H), 4.50 (s, 2H), 7.30 (m, 5H), 9.30 (s, broad, 1H).

Example 2

Hydrogenation to 1-benzyloxy-3-aminobutane
(=rac. BOBA) [Process Step (c), Scheme IV]

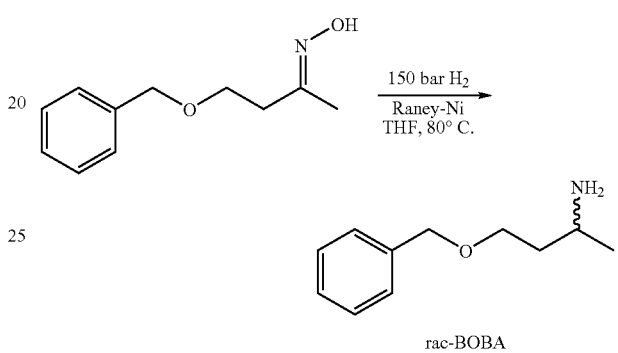

rac-BOBA

In an autoclave, 100 g of Raney nickel were initially charged in 300 ml of THF, and the mixture was admixed with a solution of 850 g (4.4 mol) of 1-benzyloxy-3-butanoneoxime in 2.5 l of THF. The autoclave was pressurized with 100 bar of hydrogen and heated with stirring to 80° C. An exothermic reaction started and the pressure was kept constant by metered addition of hydrogen gas. After the hydrogen uptake had ended, the pressure was increased to 150 bar and stirring was continued for 4 hours. The autoclave was then cooled, the stirrer was switched off and the slightly turbid product solution was decanted off from the catalyst and filtered through kieselguhr. The clear filtrate was freed from the solvent using a rotary evaporator. The less volatile residue was subsequently subjected to fractional distillation under an oil pump vacuum. At 1.3 mm/85-87° C., the product rac-BOBA distils over as a clear liquid.

Yield: 646 g (83%)

$^1$H-NMR: δ=1.05 (d, J=7 Hz; 3H), 1.35 (s, broad; 2H), 1.65 (mc; 2H), 3.10 (mc; 1H), 3.55 (mc; 2H), 4.50 (s, 2H), 7.30 (m, 5H).

Example 3

Racemate Resolution [Process Step (d)]

A. Enantiomer Analysis of BOBA:

Derivatization (Scheme V):

0.5 g of amine was dissolved in 25 ml of diethyl ether. The solution was cooled to 0° C. and 0.2 ml of benzoyl chloride was added all at once. At room temperature, the mixture was stirred for 30 minutes and then admixed with 10 ml of water. The aqueous phase was separated off and the upper, organic phase was washed successively with 10 ml each of 10% strength hydrochloric acid, water and saturated sodium bicarbonate solution. The reaction solution was dried over sodium sulfate. 1 ml of the solution was then diluted with 5 ml of n-hexane and analyzed by HPLC chromatography.

Scheme V: Derivatization

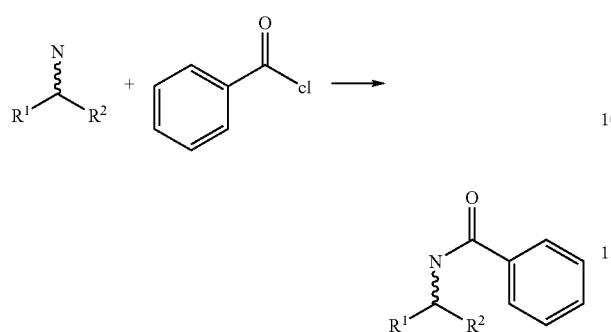

Column: Chiralcel OD
Daicel Chemical Industries, Ltd.
Temperature: room temperature
Detector: absorption at 214 nm
Amount injected: 20 μl
Mobile phase: n-hexane/isopropanol/ethanol (300:50:0.8 v/v/v)
Flow rate: 1.3 ml/min (at about 40 kg/cm$^2$)
Retention Times:

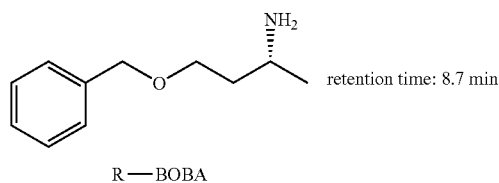

retention time: 8.7 min

R—BOBA

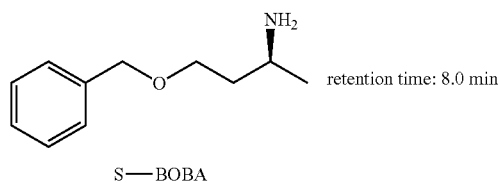

retention time: 8.0 min

S—BOBA

Example 4

Racemate Resolution by Crystallization

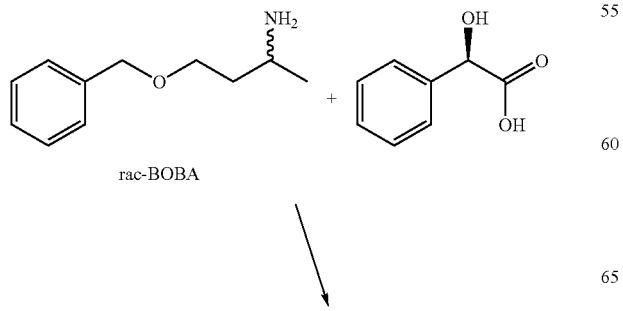

rac-BOBA

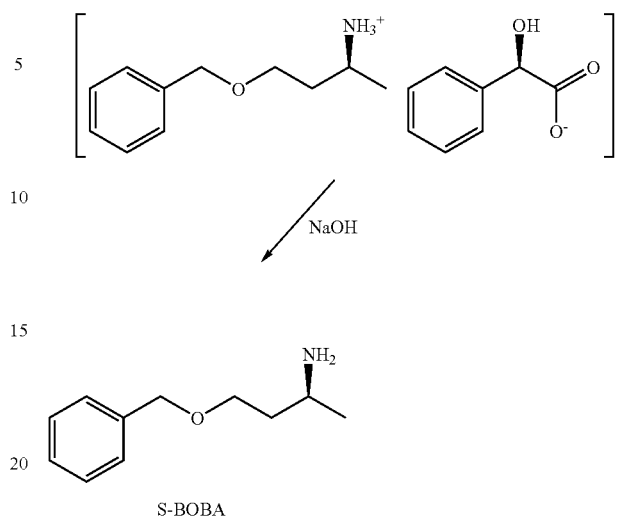

S-BOBA

A solution of 2.15 g (35.6 mmol) of acetic acid and 5.4 g (35.6 mmol) of D-mandelic acid in 50 ml of isopropanol was added dropwise to a solution of 12.8 g (71.5 mmol) of rac-BOBA in 70 ml of isopropanol. The precipitated solid was redissolved by heating and then allowed to stand for recrystallization.

From a sample of the salt, which had been filtered off with suction, the bound amine was freed by treatment with aqueous sodium hydroxide solution.

According to HPLC analysis, the S-BOBA had an ee value of 50.5%. The precipitated salt was then recrystallized once more from 100 ml of isopropanol. The amine was then freed from the resulting salt by treatment with 10 ml of 50% strength sodium hydroxide solution and extracted with 50 ml of ether, and the extract was concentrated. This gave 2.2 g (34%) of S-BOBA. According to HPLC analysis, the enantiomeric purity was 90% ee.

Example 5

Racemate Resolution by Enzyme-catalyzed Racemate Resolution

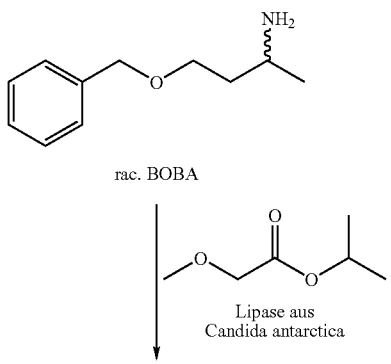

rac. BOBA

Lipase aus Candida antarctica

-continued

R-BOBamide

S-BOBA

| NaOH

R-BOBA 1500 g (8.43 mol) of rac-BOBA were cooled to 0° C. and admixed with 523 g (3.96 mol) of isopropyl methoxyacetate. 75 g of Novozym 435® were added, and the mixture was warmed with stirring to room temperature (about 23° C.). After 15 hours, the catalyst was filtered off and washed with 1 l of toluene. The filtrate was freed from volatile components under reduced pressure (20 mbar) and then distilled in a thin-film evaporator (1.0 mbar, 180° C.). S-BOBA passed over as overhead distillate at (95-98° C.), R-BOBamide went into the distillation bottom as heavy boiler.

802.5 g (53%) of S-BOBA which, according to HPLC analysis, has an optical purity of 90% ee were obtained.

964 g (45.5%) of R-BOBamide (opt. purity: 98% ee) were obtained as bottom.

R-BOBamide, $^1$H-NMR: δ=1.20 (d, J=7 Hz; 3H), 1.65-1.95 (mc; 2H), 3.15 (s; 3H), 3.50-3.70 (mc; 2H), 3.75 and 3.85 (AB system, $J_{AB}$=10.5 Hz; 2H), 4.20 (mc; 1H), 4.50 (s, 2H), 6.90 (s, broad; 1H), 7.10-7.40 (m, 5H).

Example 6

Cleavage of the R-BOBamide

R-BOBamide

NaOH

R-BOBA

At 120° C., a mixture of 918 g (3.66 mol) of R-BOBamide and 900 g of triethanolamine was admixed with 800 g (10 mol) of 50% strength sodium hydroxide solution, and the mixture was stirred at this temperature for 3 hours. After cooling, the mixture was diluted with 1.5 l of water and extracted three times with in each case 1 l of diethyl ether. The combined extracts were washed successively with 1 l of water and 100 ml of saturated NaCl solution, dried over $Na_2SO_4$ and then concentrated. This left a residue of 625 g (95%) of R-BOBA as a slightly yellow oil.

According to HPLC, the optical purity was 97% ee.

We claim:

1. A compound of the formula IX (IX)

* = optically active wherein,

R$^1$ is substituted or unsubstituted, branched or unbranched $C_1$-$C_{10}$-alkyl, $C_2$-$C_{10}$-alkenyl, $C_2$-$C_{10}$-alkynyl, arylalkyl, aryl, hetarylalkyl or hetaryl, R$^2$ is substituted or unsubstituted, branched or unbranched $C_1$-$C_{10}$-alkyl, $C_3$-$C_{10}$-alkenyl, $C_3$-$C_{10}$-alkynyl, arylalkyl, aryl, hetarylalkyl or hetaryl, R$^3$ is hydrogen, hydroxyl, substituted or unsubstituted, branched or unbranched $C_1$-$C_{10}$-alkyl, $C_3$-$C_{10}$-alkenyl or $C_3$-$C_{10}$-alkynyl, R$^5$ is hydrogen, substituted or unsubstituted, branched or unbranched $C_1$-$C_{10}$-alkyl, R$^6$ is hydrogen, substituted or unsubstituted, branched or unbranched $C_1$-$C_{10}$-alkyl or substituted or unsubstituted phenyl.

X=oxygen or nitrogen, n=0 or 1.

2. A compound of the formula IX (IX)

* = optically active obtained by a process which comprises the following process steps:

a) reaction of compounds of the formula II (II)

with compounds of the formula R$^2$—XH (III) in the presence of a base to give compounds of the formula IV

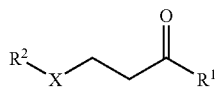
(IV)

b) reaction of compounds of the formula IV with a compound of the formula $NH_2R^3$ (V) to give compounds of the formula VI

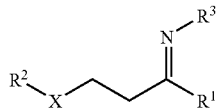
(VI)

c) hydrogenation of compounds of the formula VI in the presence of a hydrogenation catalyst to give compounds of the formula VII

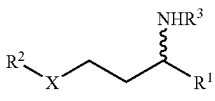
(VII)

d) resolution of a racemate of compounds of the formula VII using an optically active carboxylic acid or esters of the formula VIII

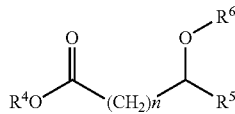
(VIII)

in the presence of a lipase or esterase to obtain a mixture of optically active heteroatom-substituted amine of the formula I

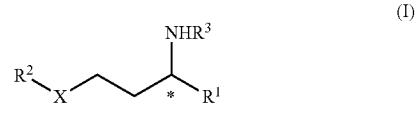
(I)

* = optically active and optically active heteroatom-substituted amide of the formula IX, and e) separation of the mixture obtained in step (d), where $R^1$ is substituted or unsubstituted, branched or unbranched $C_1$-$C_{10}$-alkyl, $C_2$-$C_{10}$-alkenyl, $C_2$-$C_{10}$-alkynyl, arylalkyl, aryl, hetarylalkyl or hetaryl, $R^2$ is substituted or unsubstituted, branched or unbranched $C_1$-$C_{10}$-alkyl, $C_3$-$C_{10}$-alkenyl, $C_3$-$C_{10}$alkynyl, arylalkyl, aryl, hetarylalkyl or hetaryl, $R^3$ is hydrogen, hydroxyl, substituted or unsubstituted, branched or unbranched $C_1$-$C_{10}$-alkyl, $C_3$-$C_{10}$-alkenyl or $C_3$-$C_{10}$-alkynyl, $R^4$ is substituted or unsubstituted, branched or unbranched $C_1$-$C_{10}$-alkyl, $R^5$ is hydrogen, substituted or unsubstituted, branched or unbranched $C_1$-$C_{10}$-alkyl, $R^6$ is hydrogen, substituted or unsubstituted, branched or unbranched $C_1$-$C_{10}$-alkyl or substituted or unsubstituted phenyl, X=oxygen or nitrogen, n=0 or 1.

* * * * *

UNITED STATES PATENT AND TRADEMARK OFFICE
CERTIFICATE OF CORRECTION

| | |
|---|---|
| PATENT NO. | : 7,358,396 B2 |
| APPLICATION NO. | : 11/327307 |
| DATED | : April 15, 2008 |
| INVENTOR(S) | : Ditrich et al. |

It is certified that error appears in the above-identified patent and that said Letters Patent is hereby corrected as shown below:

In Claim 1, col. 22, indicated line 38:
"phenyl." should read --phenyl,--

In Claim 2, col. 24, indicated line 24:
"$C_3$-$C_{10}$alkynyl" should read --$C_3$-$C_{10}$-alkynyl--

Signed and Sealed this

Eighth Day of July, 2008

JON W. DUDAS
*Director of the United States Patent and Trademark Office*